US006491426B1

(12) United States Patent
Schonath et al.

(10) Patent No.: US 6,491,426 B1
(45) Date of Patent: Dec. 10, 2002

(54) THERMAL BOND VERIFICATION

(75) Inventors: Peter Schonath, Augsburg (DE);
Steven A. F. Weller, Milpatas, CA (US)

(73) Assignee: SBS Technologies Inc., Albuquerque, NM (US)

( * ) Notice: Subject to any disclaimer, the term of this patent is extended or adjusted under 35 U.S.C. 154(b) by 0 days.

(21) Appl. No.: 09/891,627

(22) Filed: Jun. 25, 2001

(51) Int. Cl.[7] .......................... G01N 25/00; G01N 25/72
(52) U.S. Cl. ............................................. 374/45; 374/5
(58) Field of Search ................................ 374/5, 45, 43, 374/6, 7, 44

(56) References Cited

U.S. PATENT DOCUMENTS

| | | | | |
|---|---|---|---|---|
| 3,745,460 A | * | 7/1973 | Belzer et al. .................. | 374/43 |
| 4,696,578 A | * | 9/1987 | Mansuria et al. .............. | 374/45 |
| 4,713,612 A | * | 12/1987 | Takamine ..................... | 374/44 |
| 4,840,495 A | * | 6/1989 | Bonnefoy ..................... | 374/43 |
| 5,152,607 A | | 10/1992 | Ibar | |
| 5,201,841 A | * | 4/1993 | Lebeau et al. ................. | 374/5 |
| 5,211,477 A | | 5/1993 | Li | |
| 5,224,775 A | | 7/1993 | Reading et al. | |
| 5,246,291 A | * | 9/1993 | Lebeau et al. ................. | 374/5 |
| 5,251,980 A | | 10/1993 | Hiraoda et al. | |
| 5,288,147 A | | 2/1994 | Schaefer et al. | |
| 5,295,745 A | | 3/1994 | Cassettari et al. | |
| 5,302,022 A | * | 4/1994 | Huang et al. .................. | 374/44 |
| 5,474,385 A | | 12/1995 | Reading | |
| 5,721,455 A | * | 2/1998 | Takashita ..................... | 257/713 |
| 5,785,799 A | | 7/1998 | Culnane et al. | |
| 5,842,788 A | | 12/1998 | Danley et al. | |
| 6,006,168 A | | 12/1999 | Schumann et al. | |
| 6,039,471 A | * | 3/2000 | Wyland ........................ | 374/43 |
| 6,092,926 A | | 7/2000 | Still et al. | |
| 6,169,442 B1 | | 1/2001 | Meehan et al. | |
| 6,198,245 B1 | | 3/2001 | Du et al. | |
| 6,238,086 B1 | * | 5/2001 | Mikubo et al. ................ | 374/43 |

FOREIGN PATENT DOCUMENTS

FR        2643717 A  *  8/1990  ..........  G01N/25/18

OTHER PUBLICATIONS

Citarella, Joe, "Determining Heat Sink Efficiency Using Thermal Diode Temperatures," www.overclockers.com/tips32, 3 pp.

* cited by examiner

*Primary Examiner*—Diego Gutierrez
*Assistant Examiner*—Mirellys Jagan
(74) *Attorney, Agent, or Firm*—Snell & Wilmer LLP (57) ABSTRACT

A system and method for evaluating the thermal bond between a heat-producing device and a heat-absorbing apparatus. The heat-producing device may be a CPU, such as an INTEL PENTIUM microprocessor, and the heat-absorbing apparatus may be a heat sink. The two may be joined with a heat-conducting substance such as thermal grease or adhesive. In one exemplary embodiment, the heat-producing device is operated at a first power level, a first temperature measurement is then taken, the device is operated at a second power level, and then a second temperature measurement is then taken. The thermal resistance is then calculated, which may involve subtracting the second temperature from the first, and may involve dividing by the power level. The first power level may be full power, and the second power level may be near zero. The first temperature may be measured when equilibrium temperatures have been reached, and the second temperature may be measured a predetermined amount of time after the second power level is initiated, which may be just enough time for the temperatures of the CPU and the heat sink to equalize. The CPU may perform the calculations, and the temperature may be measured with an on-board thermal sensor which may be a thermal diode.

53 Claims, 5 Drawing Sheets

THERMAL BOND VERIFICATION

BACKGROUND OF THE INVENTION

1. Field of the Invention

This invention relates generally to systems and methods for evaluating thermal bonds.

2. Description of the Related Art

Many mechanical and electrical devices generate heat internally which must be dissipated to the environment to keep the devices within a range of desired operating temperatures. Such heat-producing devices may include engines, bearings, motors, power supplies, transformers, amplifiers, control modules, and computer chips and components including graphics controllers, network interfaces, and central processing units (CPUs). In some applications it is desirable to transfer heat from a heat-producing device to a heat-absorbing apparatus so that the heat may be used for useful purposes. These useful purposes may include generating electricity, providing heat for industrial processes, heating water, heating air (e.g. to heat the occupied space in buildings), or preventing freezing. Heat-absorbing apparatuses may comprise fluids which move, change phase, or both, to transfer heat, and may involve or approximate thermodynamic cycles such as a Rankine, Carnot, or Brayton cycle. On the other hand, heat-absorbing apparatuses may be simple solid devices such as heat sinks (heatsinks), for instance, typically without macroscopic moving parts.

A heat sink is one type of heat-absorbing apparatus. As an example, heat sinks have been used to cool CPUs in computers including general-purpose desk-top PCs. A heat sink is a device, typically monolithic, that conducts and usually dissipates heat. Heat sinks may be made of a metal such as aluminum or copper, or in some applications may be made of other materials such as ceramic or plastic. The heat typically travels from the heat-generating device to the heat sink primarily through conduction, and then travels through the heat sink, typically also via conduction. Heat sinks may have a large surface area to dissipate heat (e.g. large relative to the surface area of the heat-producing device), generally through convection, e.g. to surrounding air. The high surface area may be accomplished with fins, holes, hills and valleys, or other geometric features. The air may be blown with a fan to increase the Nusselt number and improve cooling, or the system may rely on natural convection. Some heat may also be transferred through radiation, particularly in high-temperature applications, and heat sinks may be configured with a surface having a high emissivity to facilitate radiant heat transfer. For instance, heat sinks may have black coatings.

Heat sinks may comprise multiple parts, e.g. multiple fins attached to the heat-producing device. In addition, e.g. in applications where heat is produced transiently, heat sinks may not have fins or other features to dissipate heat, but may rely on their bulk to absorb and store the heat produced, which may then be dissipated slowly over time. Heat sinks may also perform other functions, including acting as a structure or enclosure, or may be formed from components also used for other purposes. For instance, the housing of a distributor in an automobile may serve as a heat sink for an ignition control module (ICM) housed within the distributor. In such an application, the heat produced by the ICM may typically transfer by conduction into the distributor housing, and then by convection to the air traveling through the engine compartment of the automobile.

In order to conduct heat effectively, in many applications it is desirable to have a good thermal bond (i.e. a low thermal resistance) between the heat-producing device and the heat-absorbing apparatus so that heat will transfer relatively freely from the heat-producing device to the heat-absorbing apparatus. The quality of the thermal bond may be more important where the heat-producing device is small relative to the amount of heat that is generated within, or where the heat-producing device must be maintained at a temperature close to ambient. In typical applications where the heat-producing device and heat-absorbing apparatus are separate components and heat is transferred between them by conduction, a heat-conducting substance such as a thermal grease or thermal paste may be used between the heat-producing device and the heat-absorbing apparatus. A heat-conducting substance is typically a non-Newtonian fluid that may be tacky and flexible, at least when installed, so that it fills most of the microscopic gaps between the surfaces of the heat-producing device and heat-absorbing apparatus. The heat-conducting substance may be an adhesive or glue that holds the heat-producing device and heat-absorbing apparatus together once assembled. The heat-conducting substance may be a metal such as solder, or a thermal wax, and may be melted during the joining of the heat-producing device and heat-absorbing apparatus, but may remain solid at the normal operating temperature of the heat-producing device. A heat-conducting substance is preferably a good conductor of heat, and may be an electrical conductor so that heat conduction may occur via the movement of electrons. The surfaces of the heat-producing device and heat-absorbing apparatus may be cleaned prior to applying the heat-conducting substance in order to avoid thermal resistance from foreign materials on the surfaces, such as oxidation.

In one specific application, INTEL PENTIUM-based computers may have a heat sink attached to the top of the CPU chip which are designed to dissipate heat produced by the chip. The heat is typically dissipated to air that may be moved by fans and may ultimately be vented to the outside of the equipment case. It is typically important that the CPU be kept below a temperature that would shorten its life, cause mechanical damage, cause software to malfunction, or destroy the device completely. Systems and methods have been developed to test and evaluate the effectiveness of heat sinks, including systems and methods that use thermal sensors such as thermal diodes, which may be on-board components of the CPU chips. A properly rated heat sink with sufficient airflow can perform adequately if it is properly affixed to the CPU chip.

In many applications, it is desirable that a good thermal bond be produced between a heat-producing device and a heat-absorbing apparatus. However, as with any manufacturing process, it is difficult or expensive to verify that all items manufactured have a good thermal bond. This is particularly true where the heat-producing device has a small surface area for heat conduction, such as a flip-chip (also written flip chip or flipchip) CPU. Therefore, it would be desirable to have a convenient system and process or method to test or evaluate the thermal bond between a heat-producing device and a heat-absorbing apparatus.

For instance, it is desirable to have a convenient system and method to test the thermal bond between a computer CPU and its heat sink. During the manufacture of a computer, a heat sink may be affixed to the CPU and a path of low thermal conductivity established with a combination of thermal paste or adhesive and pressure. There is typically a relatively small area on the top of the chip that may need to have a low resistance path to the heat sink and modifications to this area (e.g. drilling to insert a temperature probe) may dramatically affect its operation. Due to the mechanical arrangement of the two parts (CPU and heat sink) as well as the complexities encountered when trying to remove heat from CPUs in confined spaces, in the past it has been difficult to verify during manufacture that the thermal bond between the CPU and the heat sink has been correctly made. Therefore, as a specific example, it would be desirable to have a convenient system and process or method to test or evaluate the thermal bond between a CPU and a heat sink.

SUMMARY OF THE INVENTION

This invention provides a system and method for evaluating the thermal bond between a heat-producing device and a heat-absorbing apparatus. In an exemplary embodiment, it provides a convenient system and process or method to test or evaluate the thermal bond between a CPU and a heat sink. Features of this invention include that it is easy and convenient to use, that in some applications it requires few or no additional parts, and that costs are therefore minimal.

In furtherance of these features, this invention provides a system for evaluating the thermal bond between a heat-producing device and a heat-absorbing apparatus which may be a heat sink. A thermal bond with a thermal resistance generally exists between the heat-producing device and the heat-absorbing apparatus. In some embodiments, a thermal sensor measures the temperature at or near the device, and a circuit or CPU is configured to perform the functions of operating the device substantially at a first power level, measuring a first temperature with the thermal sensor, operating the device substantially at a second power level, measuring a second temperature with the thermal sensor, and calculating the thermal resistance using the first temperature and the second temperature. The heat-producing device may be the circuit, and the thermal sensor may be located within the circuit. The circuit may be configured to calculate the thermal resistance by subtracting the second temperature from the first temperature, and in some embodiments, by dividing the difference by the first power level. The thermal bond may utilize a heat-conducting substance which may be thermal grease, thermal paste, thermal wax, glue, adhesive, or solder. Furthermore, the second temperature may be measured a predetermined time after the second power level is initiated.

The present invention also provides a method of evaluating the thermal bond between a heat-producing device and a heat-absorbing apparatus. In one embodiment the method includes, initiated in the following order, the steps of operating the device substantially at a first power level, measuring a first temperature of or near the device, operating the device substantially at a second power level, measuring a second temperature of or near the device, and calculating the thermal resistance of the thermal bond between the device and the apparatus. The calculating procedure may include use of at least the first temperature and the second temperature. In fact, the second power level may be less than the first power level, and the calculating procedure may involve subtracting the second temperature from the first temperature. The step of operating the device substantially at a first power level may involve operating the device until the heat-producing device and the heat-absorbing apparatus substantially reach equilibrium temperature. In addition, the step of measuring the second temperature may occur at least 10 seconds after the initialization of the step of operating the device at the second power level. In addition, the method according to the present invention may also include the step of accepting the thermal bond if the thermal resistance is below a threshold.

The present invention further provides a method of evaluating the thermal bond between a heat-producing device and a heat sink. In one embodiment, the method includes the steps of operating the device substantially at a first power level, at least until the device and the heat sink substantially reach equilibrium temperature, measuring a first temperature substantially of the device, operating the device substantially at a second power level, typically less than the first power level, and after a period of time at the second power level, measuring a second temperature, also substantially of the device. The method also usually includes calculating the thermal resistance of the thermal bond between the device and the heat sink, which may involve subtracting the second temperature from the first temperature. The method may also include the step of accepting the thermal bond if the thermal resistance is below a threshold. The device may be an integrated circuit chip, such as, for example, a CPU, and the measuring may involve using a thermal diode, which may be integral with the device.

In addition, the period of time before the second measurement is made may be a predetermined amount of time between the beginning of the operating the device at the second power level and the measuring of the second temperature. The method may further include the step of remounting the heat sink on the device if the thermal resistance is above the threshold. Remounting may involve the steps of separating the heat sink and the device, cleaning the heat sink and the device, applying or reapplying a heat-conducting substance, and reattaching the heat sink and the device. The calculating procedure may be performed by the device, and may involve dividing by the power consumption of the device. The thermal bond may utilize thermal grease, thermal paste, thermal wax, or adhesive. The second power level may be less than 10% of the first power level, and the CPU may be a flip-chip CPU. Furthermore, some embodiments include a step of measuring a third temperature at or near the device, typically measured after the second temperature, but while the device is still being operated at the second power level.

The present invention even further provides products made according to the above methods.

BRIEF DESCRIPTION OF THE DRAWINGS

The present invention is illustrated by way of example and not limitation in the accompanying figures, in which like reference numerals indicate similar elements and in which.

DETAILED DESCRIPTION OF EXEMPLARY EMBODIMENTS

This invention provides a system and method for evaluating the thermal bond between a heat-producing device and a heat-absorbing apparatus. The heat-producing device may be an electrical device such as an electrical circuit or chip, e.g. a CPU, and the heat-absorbing apparatus may be a heat sink. The heat-producing device may be attached to the heat-absorbing apparatus with a heat-conducting substance such as a thermal grease.

In an exemplary embodiment, this invention solves the problem of verifying adequate CPU-heat sink thermal conductivity for a computer that has a thermal diode mounted close to the CPU, mounted in the CPU's packaging, or integrated onto or into the chip's die. In many embodiments, no additional tools or equipment are required by the system and method described, nor is it typically necessary to remove or modify the heat sink.

The system and method typically involves operating the heat-producing device at two different power levels. The heat-producing device and heat-absorbing apparatus may be allowed to reach equilibrium temperature at the first, typically higher, power level, after which the temperature, e.g. of the heat-producing device, is measured. Next the power level of the heat-producing device is changed to a second power level, typically lower than the first, which may be at or near zero. The temperature, e.g. of the heat-producing device, is then measured again, in some embodiments after the second power level has been maintained for a predetermined amount of time. Then, the thermal resistance of the thermal bond between the heat-producing device and the heat-absorbing apparatus is calculated, for example, by subtracting the two temperatures and dividing by the first power level.

Figure 1:
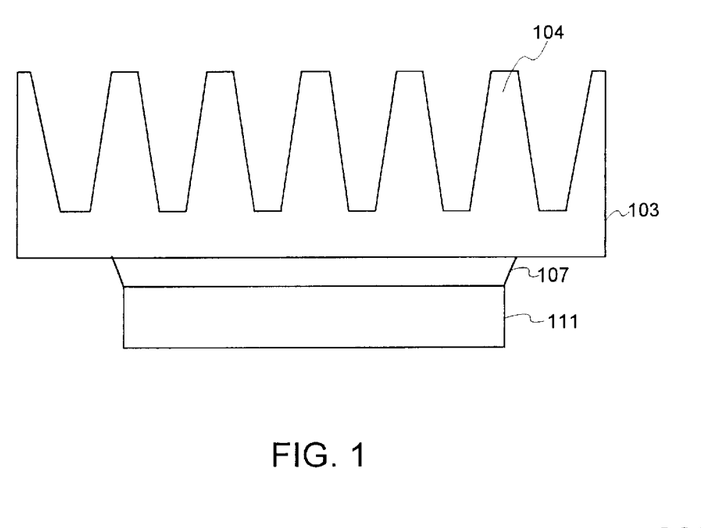
FIG. 1 is a side view schematically illustrating an exemplary bond between a heat-producing device and a heat-absorbing apparatus.
Figure 2:
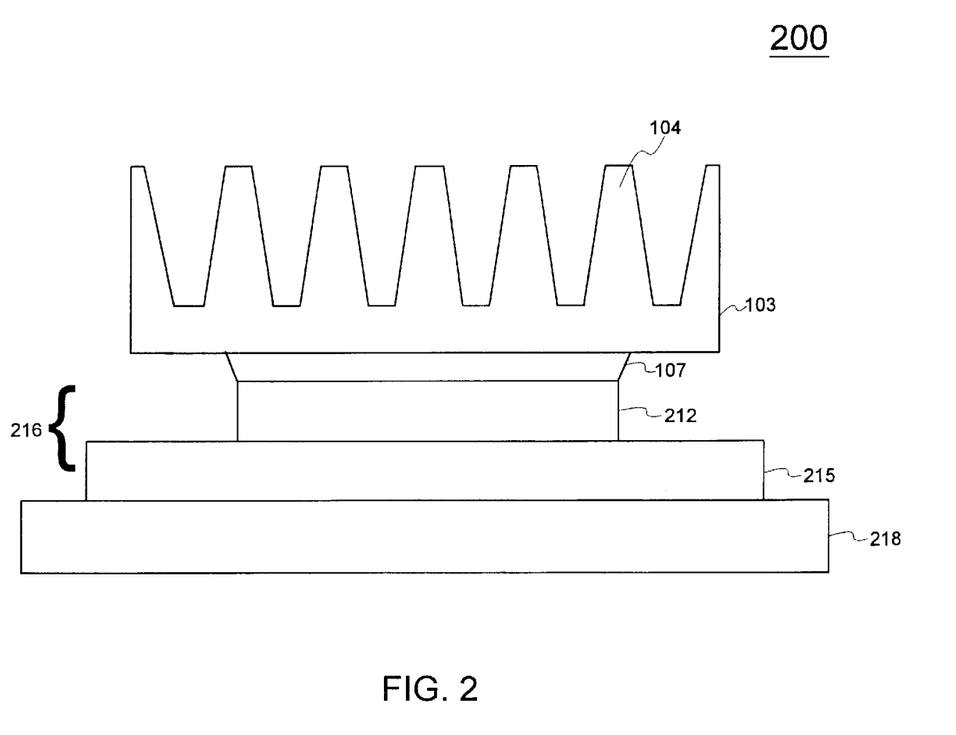
FIG. 2 is a side view schematically illustrating, as an example, the bond between a heat sink and a CPU mounted on a circuit board.
Figure 3:
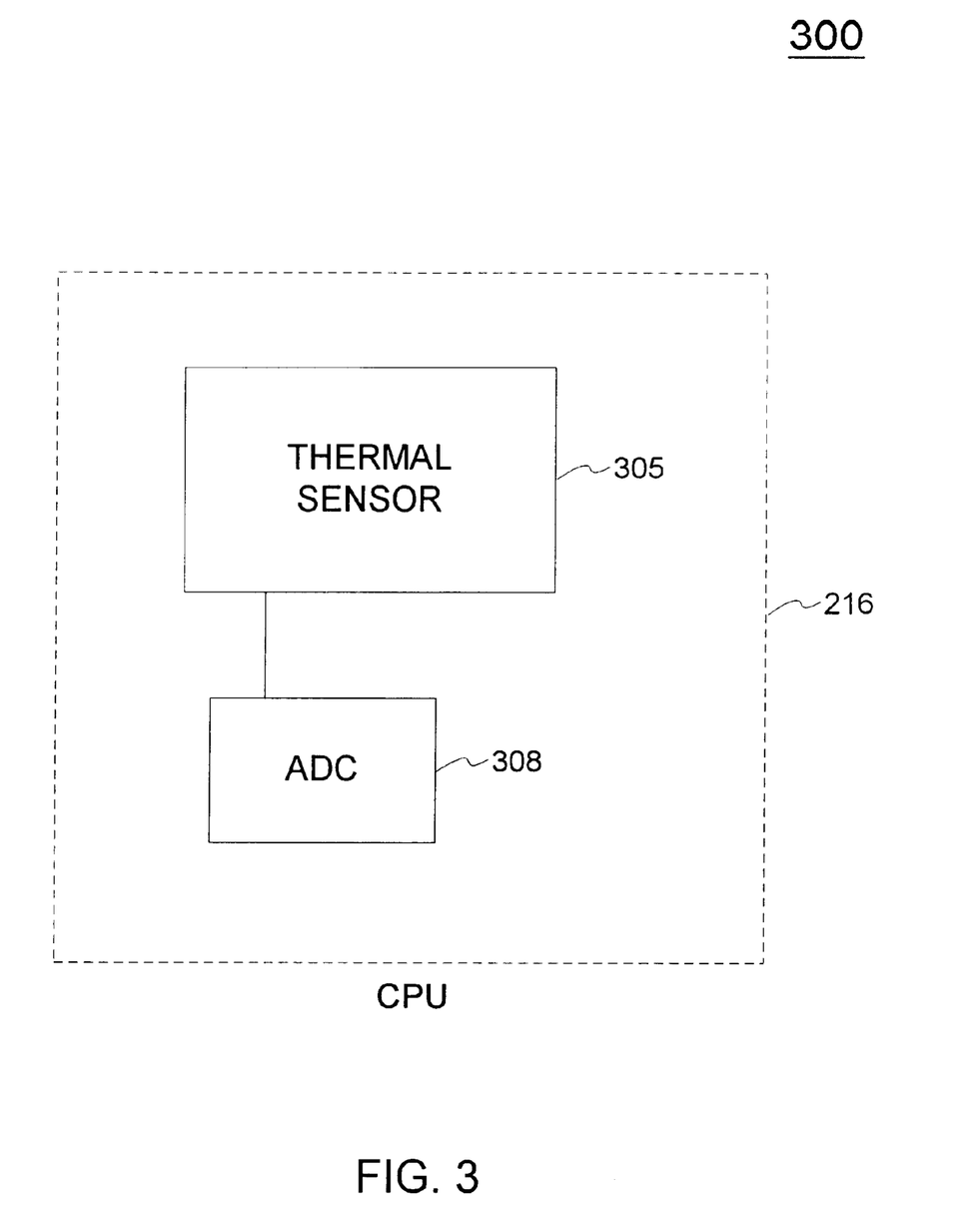
FIG. 3 is a block diagram illustrating an exemplary thermal sensor on a CPU.

Referring now to FIGS. 1 through 3, various systems according to the present invention and products made in accordance with methods described herein, will now be described in detail. Accordingly, FIG. 1 is a side view schematically illustrating the bond between a heat-producing device 111 and a heat-absorbing apparatus 103 in exemplary embodiment 100 of the present invention. In the exemplary embodiment illustrated, heat-absorbing apparatus 103 is a heat sink, having fins 104. In the embodiment wherein heat-absorbing apparatus 103 is a heat sink, heat-absorbing apparatus 103 may be a heat sink as described above or as known in the art, and may have a different shape than shown, including being a structural component or enclosure. Heat-absorbing apparatus 103 may be another type heat-absorbing apparatus, including those described above. Heat-producing device 111 may be a mechanical or electrical device as described above, such as a computer chip or CPU. The thermal bond between heat-producing device 111 and heat-absorbing apparatus 103 may be enhanced by a heat-conducting substance 107 as shown and described above. For example, heat-conducting substance 107 may be a thermal grease, thermal paste, thermal wax, or a metal such as solder. For instance, a thermal wax with a 0.12 mm cold thickness, that melts at 60° C. may be used for a typical heat-producing device 111 that is a CPU. Heat-conducting substance 107 may be a glue, adhesive, or adhesive heat glue and may physically attach heat-producing device 111 to heat-absorbing apparatus 103. Other embodiments may not have a heat-conducting substance 107, and for the required heat transfer, may rely on physical contact between a surface of heat-producing device 111 and a surface of heat-absorbing apparatus 103. In such embodiments there may be some isolating gaps between heat-producing device 111 and heat-absorbing apparatus 103, which may contain air.

In various embodiments according to the present invention, there may be more than one heat-producing device used with one heat-absorbing apparatus, or there may be more than one heat-absorbing apparatus used with one heat-producing device. For instance, a plurality of integrated circuit chips may be cooled by one heat sink, e.g. in a multichip module or microchip module (MCM).

FIG. 2 is a side view schematically illustrating the bond between a heat-absorbing apparatus 103 and a CPU 216 mounted on a circuit board such as a printed circuit board (PCB) 218 in exemplary embodiment 200 of the present invention. As described above with reference to FIG. 1, the heat-absorbing apparatus 103 illustrated is shown as a heat sink with fins 104, but may be another type heat sink including those described above or known in the art, or may be another type heat-absorbing apparatus. CPU 216 may be a flip-chip CPU as shown, and may be a flip-chip pin grid array (FC-PGA) or a ball grid array (BGA). Thermal solutions may be attached directly to the back of the processor core package without the use of a thermal paste or heat spreader. CPU 216 may be comprised of CPU silicon die 212 and die carrier 215 as shown, which may be attached in ways known in the art. Silicon die 212 may be flipped (top down) on a substrate containing the solder balls or pins, and directly soldered, glued, or both, to it, typically by the chip manufacturer. In other words, silicon die 212 may be a flip chip. Silicon die 212 and die carrier 215 may form flip-chip CPU 216. CPU 216 may be mounted on PCB 218. CPU 216 is generally one type of heat-producing device (e.g. heat-producing device 111 shown in FIG. 1).

A thermal sensor is typically located integral with, in contact with, or near, heat-producing device 111 or CPU 216. Accordingly, FIG. 3 is a block diagram illustrating a thermal sensor 305 on a CPU 216 in exemplary embodiment 300 of one aspect of the present invention. Although in the example shown, CPU 216 is a CPU, it may be another heat-producing device, e.g. heat-producing device 111 in FIG. 1. Thermal sensor 305 may be a thermal diode, a thermocouple, a thermistor, a resistance temperature detector (RTD), and infrared temperature measuring device, a thermometer, or any other device or system suitable for measuring temperature. CPU 216 may also have an analog to digital converter (ADC) 308 connected to thermal sensor 305 that may be read by CPU 216 and used to provide temperature readings, e.g. with a resolution of 1° C. and accuracy of +/-2° C. Although thermal sensor 305 and ADC 308 are shown being on-board or integral with CPU 216, either or both may be external to CPU 216 or to the heat-producing device (111). Thermal sensor 305 is generally configured and located near enough to substantially measure the temperature of heat-producing device 111. Thermal sensor 305 may be located at or near CPU 216 (or heat-producing device 111), or may be at some distance away, and measure the temperature of CPU 216, e.g. by sensing infrared radiation emitted by CPU 216. For instance, thermal sensor 305 may be mounted close to the CPU, mounted in the CPU's packaging, or integrated onto the chip's die, e.g. into CPU silicon die 212. Thus, in various exemplary embodiments, thermal sensor 305 may be on or near the surface of CPU 216, or referring to FIGS. 1 and 2, may be in, on, or near (e.g. close enough to adequately detect the temperature of) heat-absorbing apparatus 103, heat-conducting substance 107, heat-producing device 111, CPU 216, CPU silicon die 212, die carrier 215, or PCB 218. ADC 308 may, as an example, be mounted on PCB 218.

Figure 4:
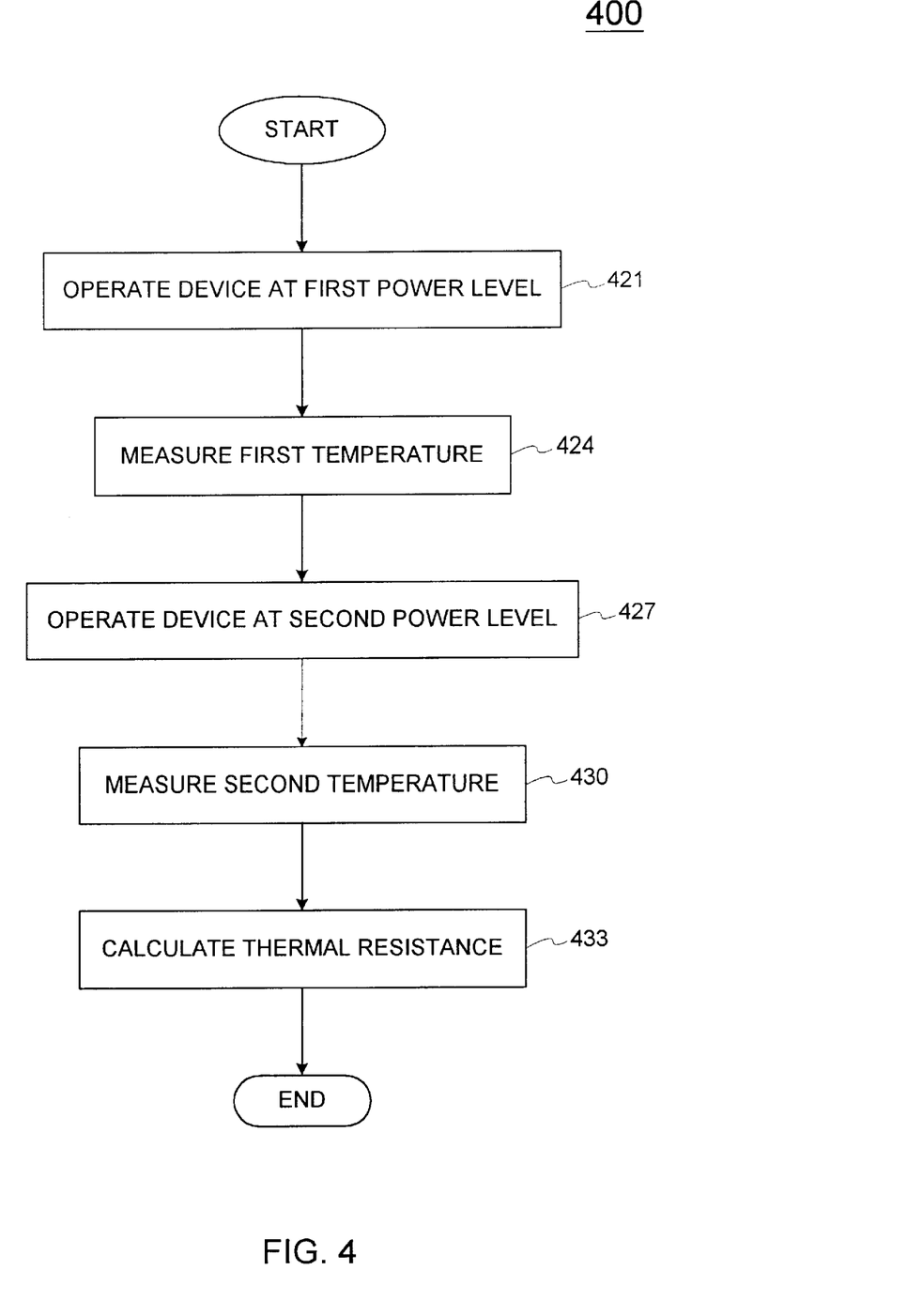
FIG. 4 is a flow chart illustrating the steps in an exemplary method according to the present invention of evaluating the thermal bond between a heat-producing device and a heat-absorbing apparatus.
Figure 5:
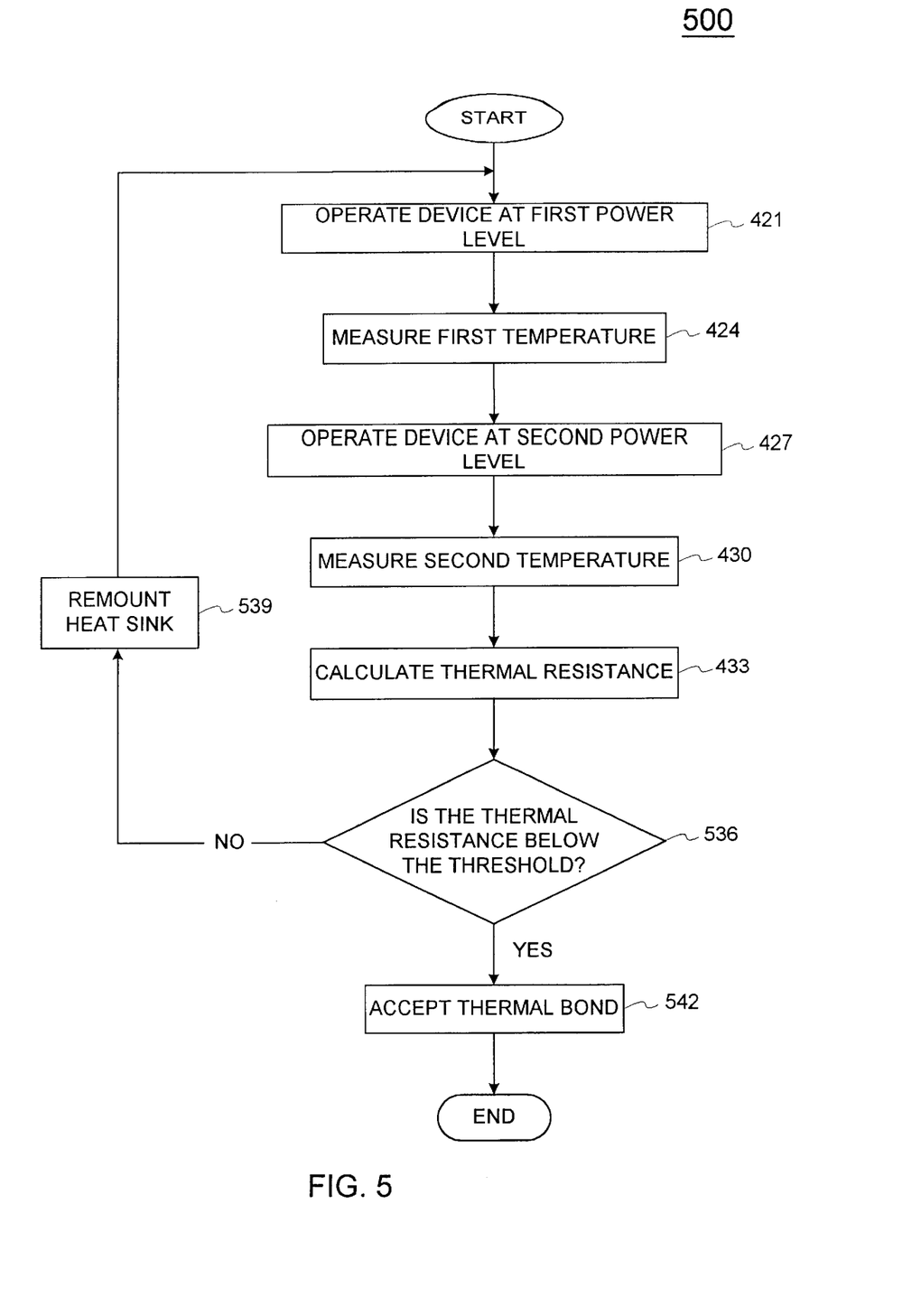
FIG. 5 is a flow chart illustrating the steps in an exemplary method according to the present invention of evaluating the thermal bond between a heat-producing device and a heat sink, and remounting the heat sink if the thermal resistance of the bond is below a threshold of acceptability.

Referring now to FIGS. 4 and 5, various methods according to the present invention for evaluating the thermal bond between a heat-producing device (e.g. 111) and a heat-absorbing apparatus (e.g. 103) will now be described, with frequent reference to the systems, products, and components illustrated in the previous figures and described above. The steps according to the methods described herein may generally be performed, initiated, or controlled by various components including electrical circuits, microprocessors, CPUs, computers and the like, and may be performed automatically, in whole or in part. Accordingly, FIG. 4 is a flow chart illustrating the steps in exemplary method 400 according to the present invention of evaluating the thermal bond between a heat-producing device (e.g. 111 in FIG. 1) and a heat-absorbing apparatus (e.g. 103 in FIG. 1).

Typically initiated first, the heat-producing device (e.g. 111) is operated at a first power level (step 421). The first power level may at or near the maximum sustainable power level of the heat-producing device (e.g. 111), or may be a typical operating power level, e.g. of heat-producing device 111. For instance, in embodiments where heat-producing device 111 is a CPU (e.g. 216), the first power level may involve CPU 216 doing some arithmetic operation, e.g. repeatedly, or may involve just waiting for keyboard input. Thus, the first power level may be a substantially constant power level, generally resulting in a substantially constant equilibrium temperature.

Heat-producing device (e.g. 111) may be operated at the first power level until equilibrium temperatures are reached, i.e. the temperatures of heat-producing device 111, heat-absorbing apparatus 103, or both, level off or stop changing. For instance, equilibrium may be recognized by monitoring thermal sensor 305 over time and noting when the temperature indicated stops increasing. As an example, CPU 216 may be operated at full speed for long enough that CPU 216 and heat sink or heat-absorbing apparatus 103 reach their equilibrium temperature, which may be established by the leveling off of the reading produced by thermal sensor 305. In other embodiments, it may not be necessary or desirable to operate the heat-producing device (e.g. 111) at the first power level (step 421) long enough to reach equilibrium temperature.

Typically initiated next, the first temperature is measured (step 424). The first temperature may be measured while the heat-producing device (e.g. 111) is still operating at the first power level (i.e. during step 421). Alternatively, the first temperature measurement may be concurrent with or after, e.g. immediately after, the termination of the operating the heat-producing device (e.g. 111) at the first power level (e.g. step 421). Measurement of the first temperature maybe triggered by the reaching of equilibrium temperature (e.g. at thermal sensor 305), passage of a predetermined amount of time, by the reaching of a particular temperature (e.g. at thermal sensor 305), or by some combination of these. Since the heat sink or heat-absorbing apparatus 103 is dissipating the heat, the die 212 or heat-producing device 111 temperature will typically be slightly above the heat sink or heat-absorbing apparatus 103 temperature. The thermal resistivity, e.g. of the CPU-heat sink bond, may determine this temperature difference. The first temperature may be recorded, for instance in a computer memory, which may be in CPU 216.

The temperature measurements (e.g. in steps 424 and 430) may be made with thermal sensor 305, which may be via ADC 308. In some embodiments, thermal sensor 305 may be non-linear, and there may be a translation step from the number read from ADC 308 (or chip register, e.g. of CPU 216) to get an actual temperature (or relative temperature). This may be carried out using a look-up table or a polynomial equation, and may be performed by CPU 216.

Typically initiated next, the power level of the heat-producing device (e.g. 111) is changed, and the heat-producing device is operated at a second power level (step 427). The second power level may be below the first power level (of step 421) and may be less than 10% of the first power level, or even at or near zero (e.g. approximately 1% of the first power level). In other words, heat-producing device may be turned off (i.e. not operating at all) or reduced to an idle mode for the second power level (step 427). For instance, using software, CPU 216 may be essentially stopped so that the heat production within falls close to zero. The operation of the heat-producing device at the second power level (step 427) typically starts after the operation of the device at the first power level (step 421) and may start after or concurrently with the measurement of the first temperature (step 424).

Typically initiated next, the second temperature is measured (step 430). The second temperature may also be measured with thermal sensor 305, and may be measured while the heat-producing device (e.g. 111) is still operating at the second power level (i.e. during step 427). Alternatively, the second temperature measurement may be concurrent with or after, e.g. immediately after, the termination of the operating the heat-producing device (e.g. 111) at the second power level (e.g. step 427). Measurement of the second temperature may be triggered by the reaching of equilibrium temperature (e.g. at thermal sensor 305), passage of a predetermined amount of time, by the reaching of a particular temperature (e.g. at thermal sensor 305), by the equalization or near equalization of the temperatures of heat-producing device 111 and heat-absorbing apparatus 103, by a decreased rate of change of the temperature, or by some combination of these. The second temperature may be recorded, for instance in a computer memory, e.g. in CPU 216.

Figure 6:
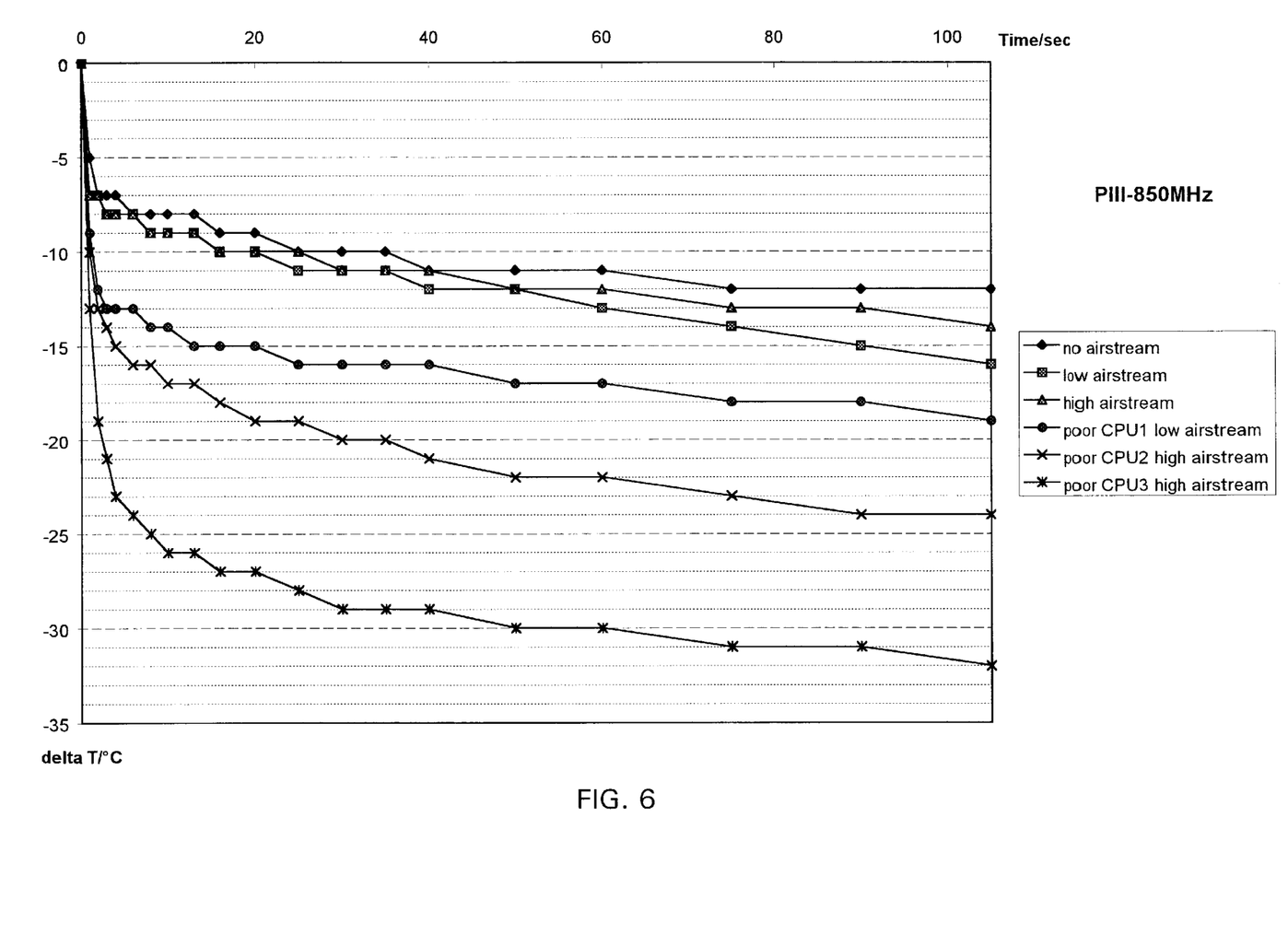
FIG. 6 is a graph illustrating as an example, how the temperature of a 850 MHz INTEL PENTIUM III microprocessor may change over time after the power level is reduced from approximately full power to idle.

As an example, FIG. 6 illustrates how the temperature of heat-producing device 111 or CPU 216 may change over time after the initiation of a lower second power level (step 427). For the exemplary embodiment which is the subject of FIG. 6, heat-producing device 111 or CPU 216 was a 850 MHz INTEL PENTIUM III microprocessor operated under the six different conditions indicated. Its temperature was measured with an on-board thermal diode and read with an on-board ADC. The heat-absorbing apparatus 103 was a heat sink. In this example, the first power level (step 421) was approximately the full power of the CPU (around 16 W when operated at 850 MHz), and the second power level was near zero (idle). As can be seen, the temperature of the CPU changed (dropped) quickly for the first 2 to 10 seconds, and then almost leveled off, but still changed (dropped) gradually after 100 seconds, e.g. asymptotically approaching equilibrium with the environment under the second power level. During the initial period of rapid temperature change, the heat was still transferring from the CPU to the heat sink. However, during the later period of gradual or asymptotic temperature change, the CPU and heat sink reached equilibrium temperature with respect to each other (in this case probably the same temperature, collectively a Biot body), but continued to cool together asymptotically as heat dissipated to the environment.

Various embodiments of the present invention involve waiting a period of time from the beginning of the period of operation at the second power level (the beginning of step 427) and the measuring of the second temperature (step 430). A predetermined amount of time may be chosen for the period of time between the beginning of the period of operation at the second power level (the beginning of step 427) and the measuring of the second temperature (step 430). For instance, as can be seen in FIG. 6, a predetermined amount of time, such as 20 seconds, may be selected that does not allow the entire assembly to cool too much, but gets past the initial period of rapid drop in temperature. A shorter predetermined amount of time, such as 10 or 12 seconds may work, particularly if the ADC has a short response time, e.g. giving results every second rather than every four seconds. Thus, as shown in FIG. 6, the first temperature may be the temperature at time zero (e.g. the reference temperature of zero degrees shown on FIG. 6). The second temperature may be, for example, the temperature at the time of 20 seconds. Other periods of time, which may be predetermined amounts of time, may be desirable for other heat-producing devices and heat-absorbing apparatuses.

To verify that a sufficient period of time has passed for the heat-producing device 111 and heat-absorbing apparatus 103 to reach the same temperature, or to verify that the initial period of rapid temperature change (e.g. as shown on FIG. 6) has ended, a third temperature may be measured which may be similar to the second temperature measurement and may also be measured with thermal sensor 305. The third temperature measurement may take place while the heat-producing device 111 is still being operated at the second power level (step 427), or may be after, e.g. immediately after, the termination of the operating the heat-producing device (e.g. 111) at the second power level (e.g. step 427). Measurement of the third temperature may, inter alia, also be triggered by the passage of a (second) period of time (e.g. after measurement of the second temperature), which may be predetermined, or measurement of the third temperature may be triggered by the reaching of a particular temperature (e.g. at thermal sensor 305). The third temperature may also be recorded, for instance in a computer memory, e.g. in CPU 216. Additional temperature measurements may be taken in a similar manner, e.g. at regular intervals of time. The taking of third or additional temperature measurements may provide confirmation that the temperature change is asymptotic or not too great at the second temperature measurement, e.g. due to different system characteristics such as a really bad thermal joint. Thus, the taking of third or additional temperature measurements may improve the accuracy of the present invention, particularly where it is desirable to evaluate thermal bonds over a wide or unpredictable range of thermal resistances.

Referring once again to FIG. 4, typically initiated next, the thermal resistance (e.g. of the thermal bond between heat-producing device 111 and heat-absorbing apparatus 103) is calculated (step 433). The thermal resistance may be calculated, for example, by subtracting the second temperature (measured in step 430) from the first temperature (measured in step 421), and dividing by the power level of the heat-producing device (e.g. 111), which may be the first power level (e.g. of step 421) or an average power level of the heat-producing device, e.g. from the manufacturer's specifications. In general, the poorer the bond between the heat-producing device and the heat-absorbing apparatus, the greater the difference between the first temperature and the second temperature. Subtracting the two temperatures also eliminates inaccuracy by subtracting out any consistent error. In fact, the first and second temperature measurements need not be absolute or conventional temperature measurements. Rather they may be relative to some reference temperature, e.g. relative to the first temperature as illustrated in FIG. 6. In addition, the greater the power level (e.g. the first power level) the greater the temperature difference as well. Therefore, the above calculation provides a good indication of the thermal resistance of the thermal bond between the heat-producing device (e.g. 111) and the heat-absorbing apparatus (e.g. 103). Other formulas may be desirable in particular circumstances, which may use some or all of the calculations described herein. The calculation of the thermal resistance (step 433) may be performed by an electrical circuit, such as a microprocessor, which may be CPU 216.

In embodiments where a third temperature measurement is taken, the difference between the third temperature and the second temperature may be calculated. If the difference is below a second threshold, as an example, then the thermal resistance may be calculated as described above using the first and second temperatures. If the difference is above the second threshold, then, as examples, the third temperature measurement may be used in the calculation described above (step 433) instead of the second temperature measurement. In embodiments having more than three temperature measurements, subsequent temperature measurements may be used similarly.

FIG. 5 is a flow chart illustrating the steps in an exemplary method according to the present invention for evaluating the thermal bond between a heat-producing device (e.g. 111) and a heat sink (e.g. one embodiment of heat-absorbing apparatus 103), including remounting the heat sink if the thermal resistance of the bond is below a threshold of acceptability. In addition to steps 421, 424, 427, 430, and 433 described above with reference to FIG. 4, FIG. 5 includes the step of evaluating the acceptability of the thermal bond (step 536). In one embodiment, which is illustrated in FIG. 5, the thermal bond is considered to be acceptable if the thermal resistance of the bond is less than a certain threshold value. The threshold value may be calculated, determined empirically, or some combination thereof. As an example, where a thermal wax is used between a CPU and a heat sink (i.e. as described in FIG. 6), the calculated thermal resistance may be 0.86° K/W. However, based on experience, the acceptable threshold thermal resistance may be selected to be 1.2° K/W to limit the maximum temperature difference to acceptable parameters (e.g. 20° K) while allowing as many CPU's as possible to be accepted. If the thermal resistance is below the threshold, then the bond may be accepted (step 542). If the thermal resistance is above the threshold, then the bond may be rejected, and the heat sink (or heat-absorbing apparatus 103) may be remounted (step 539).

Remounting a heat sink (step 539) may involve separating the heat sink and the device, cleaning the mounting surfaces of the heat sink and the device (e.g. of any heat-conducting substance, oxidation, or other foreign substances) applying (or reapplying) a heat-conducting substance (e.g. as described herein), and reattaching the heat sink to the device. Other embodiment heat-absorbing apparatuses may be remounted in a similar manner. Once the heat sink is remounted, the method of the present invention may be performed again to verify that the new thermal bond is acceptable. In alternative (or in addition) to remounting, devices with rejected thermal bonds may be discarded, recycled, or classified or used for a purpose for which they are suitable, such as lower power level applications (e.g. lower speeds), or operation in cooler or better ventilated environments. In addition, mounting methods, cleaning methods, and heat-conducting substances may be adjusted or changed, and the present invention may be used to evaluate whether the changes are effective or desirable.

The methods according to the present invention may be performed once after heat-producing device 111 is joined with heat-absorbing apparatus 103, after final assembly, before shipping, or at other times. For instance, the thermal bond may be evaluated once at the customer site, or periodically, to monitor the integrity of the thermal bond between heat-producing device 111 and heat-absorbing apparatus 103. For instance, in applications where the heat-producing device is a CPU (e.g. 216) that contains the thermal sensor (e.g. 305), the method according to the present invention may be performed periodically, and the operator may be alerted if the thermal bond has deteriorated, e.g. below a threshold. For instance, a method of the present invention may be performed when the computer is restarted after being improperly shut down. In addition, or alternatively, it may be performed whenever the device happens to be operated at a high power level until equilibrium temperatures are substantially obtained, and then it happens to be operated in an idle mode for the predetermined amount of time. In other circumstances, it may be desirable to perform the methods according to the present invention only on a sample of products.

Although the subject application has been described herein with reference to the appended drawing figures, it will be appreciated that the scope of the invention is not so limited. Various modifications in the design and implementation of various components and method steps discussed herein may be made without departing from the spirit and scope of the invention, as set forth in the appended claims.

What is claimed is:

1. A system for calculating a thermal resistance of a thermal bond between a heat-producing device and a heat-absorbing apparatus, said system comprising:
    a heat-producing device;
    a heat-absorbing apparatus;
    a thermal bond between said device and said apparatus, said thermal bond having a thermal resistance;
    a thermal sensor configured to measure the temperature at or near said device; and
    a circuit configured to;
    operate said device substantially at a first power level;
    measure a first temperature with said thermal sensor;
    operate said device substantially at a second power level;
    measure a second temperature with said thermal sensor; and
    calculate the thermal resistance using the first temperature and the second temperature.
2. The system according to claim 1, said circuit being configured to calculate the thermal resistance by subtracting the second temperature from the first temperature and dividing the difference by the first power level.
3. The system according to claim 1, said thermal bond comprising a heat-conducting substance, said heat-conducting substance being selected from the group consisting of thermal grease, thermal paste, thermal wax, glue, adhesive, and solder.
4. The system according to claim 1, said apparatus consisting of a heat sink.
5. The system according to claim 1, said circuit being configured so that the second temperature is measured a predetermined time after the second power level is initiated.
6. The system according to claim 1:
    said circuit being configured to calculate the thermal resistance by subtracting the second temperature from the first temperature and dividing the difference by a power level;
    said thermal bond comprising a heat-conducting substance thermally bonding said device to said apparatus, the heat-conducting substance being selected from the group consisting of thermal grease, thermal paste, thermal wax, and adhesive;
    said apparatus consisting of a heat sink; and
    said circuit being configured so that the second temperature is measured a predetermined time after the second power level is initiated.
7. The system according to claim 1;
    said circuit comprising a CPU; and
    said heat-producing device comprising said CPU.
8. The system according to claim 7, said CPU comprising said thermal sensor.
9. The system according to claim 7, said CPU being configured to calculate the thermal resistance by subtracting the second temperature from the first temperature and dividing the difference by the first power level.
10. The system according to claim 7, said thermal bond comprising a heat-conducting substance, said heat-conducting substance being selected from the group consisting of thermal grease, thermal paste, thermal wax, glue, adhesive, and solder.
11. The system according to claim 7, said apparatus consisting of a heat sink.
12. The system according to claim 7, said CPU being configured so that the second temperature is measured a predetermined time after the second power level is initiated.
13. The system according to claim 7,
    said CPU comprising said thermal sensor;
    said CPU being configured to calculate the thermal resistance by subtracting the second temperature from the first temperature and dividing the difference by a power level;
    said thermal bond comprising a heat-conducting substance thermally bonding said device to said apparatus, said heat-conducting substance being selected from the group consisting of thermal grease, thermal paste, thermal wax, and adhesive;
    said apparatus consisting of a heat sink; and
    said CPU being configured so that the second temperature is measured a predetermined time after the second power level is initiated.
14. A method of evaluating a thermal bond between a heat-producing device and a heat-absorbing apparatus, said method comprising, initiated in the following order, the steps of:
    operating the device substantially at a first power level;
    measuring a first temperature at or near the device;
    operating the device substantially at a second power level;
    measuring a second temperature at or near the device;
    calculating the thermal resistance of the thermal bond between the device and the apparatus, said calculating comprising using the first temperature and the second temperature; and
    evaluating the thermal bond based on the calculated thermal resistance.
15. The method according to claim 14, the step of operating the device at a first power level comprising operating the device at a substantially constant power level until the device and the apparatus substantially reach equilibrium temperatures.

16. The method according to claim 14, said step of measuring the second temperature occurring at least 10 seconds after the initialization of said step of operating the device at the second power level.

17. The method according to claim 14, said step of evaluating the thermal bond further comprising the step of accepting the thermal bond if the thermal resistance is below a threshold.

18. The method according to claim 14, said device being a an integrated circuit chip.

19. The method according to claim 14, said calculating being performed by the device.

20. The method according to claim 14, said calculating comprising dividing a temperature difference between the first and second temperatures by the power consumption of the device.

21. The method according to claim 14, the thermal bond comprising a material selected from the group consisting of thermal grease, thermal paste, thermal wax, and adhesive.

22. The method according to claim 14, the device comprising a flip chip.

23. The method according to claim 14,
the second power level being less than the first power level; and
said calculating comprising subtracting the second temperature from the first temperature.

24. The method according to claim 23, said step of measuring the second temperature occurring at least 10 seconds after the initialization of said step of operating the device at the second power level.

25. The method according to claim 23, said step of evaluating the thermal bond further comprising the step of accepting the thermal bond if the thermal resistance is below a threshold.

26. The method according to claim 23, the device being a an integrate ted circuit chip.

27. A method of evaluating a thermal bond between a heat-producing device and a heat sink, said method comprising the steps of:
operating the device substantially at a first power level at least until the device and the heat sink substantially reach equilibrium temperature;
measuring a first temperature at or near the device, substantially at the equilibrium temperature;
operating the device substantially at a second power level, the second power level being less than the first power level;
after a period of time at the second power level, measuring a second temperature at or near the device;
calculating the thermal resistance of the thermal bond between the device and the heat sink, said calculating comprising subtracting the second temperature from the first temperature and dividing the difference between the first and second temperatures by the first power level; and
accepting the thermal bond if the thermal resistance is below a threshold.

28. The method according to claim 27, the device comprising a CPU.

29. The method according to claim 27, the period of time being a predetermined amount of time between the beginning of said operating the device at the second power level and said measuring a second temperature.

30. The method according to claim 27, said calculating being performed by the device.

31. The method according to claim 27, the thermal bond comprising a material selected from the group consisting of thermal grease, thermal paste, thermal wax, and adhesive.

32. The method according to claim 27, the second power level being less than 10% of the first power level.

33. The method according to claim 27, the device comprising a flip chip.

34. The method according to claim 27 further comprising the step of measuring a third temperature at or near the device, the third temperature being:
measured after said step of measuring the second temperature; and
measured after a second period of time while the device is at the second power level.

35. The method according to claim 27,
said measuring comprising using a thermal sensor;
the thermal sensor being integral with the device;
the period of time being a predetermined amount of time between the beginning of said operating the device at the second power level and said measuring a second temperature;
the period of time being greater than 2 seconds;
the period of time being less than 100 seconds; and
the thermal bond comprising a material selected from the group consisting of thermal grease, thermal paste, thermal wax, and adhesive.

36. The method according to claim 27, said measuring the first or second temperatures comprising using a thermal diode.

37. The method according to claim 36 the thermal diode being integral with the device.

38. The method according to claim 27, further comprising the step of remounting the heat sink on the device if the thermal resistance is above the threshold.

39. The method according to claim 38, said step of remounting comprising the steps of:
separating the heat sink and the device;
cleaning the heat sink;
cleaning the device;
applying or reapplying a heat-conducting substance; and
reattaching the heat sink and the device.

40. A method of evaluating the thermal bond between an integrated circuit device and a heat sink, said method comprising the steps of:
operating the device substantially at a first power level until the device and the heat sink substantially reach equilibrium temperature, the device comprising an integrated circuit;
measuring a first temperature substantially of the device;
operating the device substantially at a second power level, the second power level being less than the first power level;
after a period of time at the second power level, measuring a second temperature substantially of the device;
calculating the thermal resistance of the thermal bond between the device and the heat sink, said calculating comprising subtracting said second temperature from said first temperature and dividing the difference between the first and second temperatures by the first power level; and
accepting the thermal bond if the thermal resistance is below a threshold.

41. The method according to claim 40, the period of time being a predetermined amount of time between the beginning of said operating the device at the second power level and said measuring a second temperature.

42. The method according to claim 40, said calculating being performed by the device.

43. The method according to claim 40, the thermal bond comprising a material selected from the group consisting of thermal grease, thermal paste, thermal wax, and adhesive.

44. The method according to claim 40, the second power level being less than 10% of the first power level.

45. The method according to claim 40, the device comprising a flip chip.

46. The method according to claim 40 further comprising the step of classifying for lower power level applications the devices having a thermal resistance above the threshold.

47. The method according to claim 40, further comprising the step of remounting the heat sink on the device if the thermal resistance is above the threshold.

48. The method according to claim 47, said step of remounting comprising the steps of:

separating the heat sink and the device;

cleaning the heat sink;

cleaning the device;

applying or reapplying a heat-conducting substance; and reattaching the heat sink and the device.

49. The method according to claim 40, the device comprising a CPU.

50. The method according to claim 49, said measuring comprising using a thermal sensor;

the thermal sensor being integral with the device;

the period of time being a predetermined amount of time between the beginning of said operating the device at the second power level and said measuring a second temperature;

the period of time being greater than 2 seconds;

the period of time being less than 100 seconds;

said calculating being performed by the device; and the thermal bond comprising a material selected from the group consisting of thermal grease, thermal paste, thermal wax, and adhesive.

51. The method according to claim 49 further comprising the step of measuring a third temperature substantially of the device, the third temperature being:

measured after said step of measuring the second temperature; and measured while the device is being operated at the second power level.

52. The method according to claim 49, said measuring comprising using a thermal diode.

53. The method according to claim 52 the thermal diode being integral with the device.

* * * * *